United States Patent [19]

Vorozhtsov et al.

[11] 4,336,383
[45] Jun. 22, 1982

[54] 1-1-BINAPHTHYL-4,4′,5,5′,8,8′-HEXACARBOXYLIC ACID COMPOUNDS, METHOD OF PREPARATION AND USE THEREOF FOR THE SYNTHESIS OF ASYMMETRIC DERIVATIVES OF 3,4,9,10-PERYLENETETRACARBOXYLIC ACID, AND FOR DYEING AND PRINTING OF TEXTILE MATERIALS

[76] Inventors: Georgy N. Vorozhtsov, Sadovo-Spasskaya ulitsa, 21, kv. 268; Natalia N. Masanova, prospekt Mira, 118-a, kv. 174; Nikolai B. Feldbljum, Bolshoi Golovin pereulok, 12, kv. 10, all of Moscow; Vasily I. Alexeev, ulitsa Mendeleeva, 33-b, kv. 83, Rubezhnoe; Vadim A. Shigalevsky, propspekt Kirova, 26, kv. 60, Rubezhnoe; Georgy G. Solomatin, prospekt Kirova, 10-b, kv. 16, Rubezhnoe; Olga I. Shulepova, prespekt Kirova, 30-49, Rubezhnoe; Galina G. Khaitun, ulitsa Krasny Kazanets 17-I27; Nadezhda V. Gordeeva, prospekt Vernadskogo, 89 kerpus, 5, kv 45, both of Moscow, all of U.S.S.R.

[21] Appl. No.: 147,600

[22] Filed: May 7, 1980

[51] Int. Cl.³ ............... C07D 519/00; C07D 487/06; C07D 487/16; C07D 487/22
[52] U.S. Cl. .................................. 546/52; 546/27; 546/29; 8/657; 8/568
[58] Field of Search ........................... 546/52

[56] References Cited

U.S. PATENT DOCUMENTS 4,166,181  8/1979  Dokunikhin .................... 546/52

FOREIGN PATENT DOCUMENTS 2134534  12/1972  France ........................ 546/52

Primary Examiner—Mark L. Berch
Attorney, Agent, or Firm—Lilling & Greenspan

[57] ABSTRACT 1,1′-Binaphthyl-4,4′,5,5′,8,8′-hexacarboxylic acid compounds having the following formula:

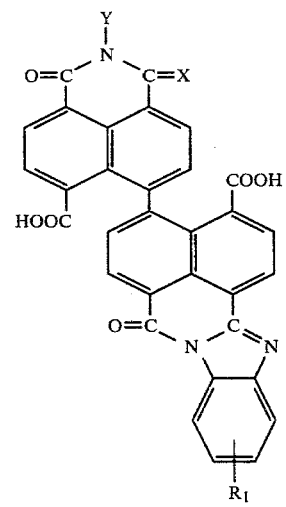

wherein $R_1$ is hydrogen, halogen, or alkyl; when X is oxygen, Y is hydrogen, alkyl, a cycloalkyl, or an aryl containing at least one substituent from the group including: halogen, alkyl, or alkoxy, when X is nitrogen, Y is

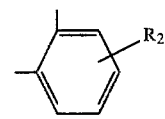

wherein $R_2$ is hydrogen, halogen, or alkyl; Y being linked to X with the formation of a benzimidazole cycle.

The method for preparing the compounds according to the present invention resides in the treatment of that 1,1′-binaphthyl-4,4′,5,5′,8,8′-hexacarboxylic acid anhydride with an alkali to give a corresponding salt which is condensed with orthophenylenediamines upon heating at reflux at a pH of from 6.3 to 6.8. The resulting benzimidazole-1,1′-binaphthyl-4,4′,5,5′,8,8′-hexacarboxylic acid anhydride having the formula:

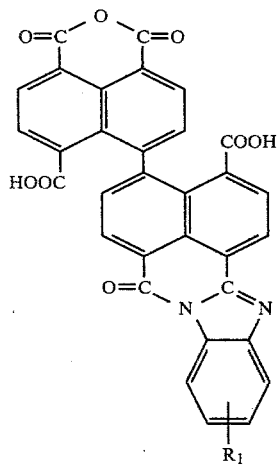

wherein $R_1$ is hydrogen, halogen, or alkyl, is isolated and condensed with an amine or ortho-phenylenediamines in an excess of the amine, in water or an organic solvent, followed by isolation of the desired product.

The compounds according to the present invention are employed for the synthesis of asymmetric compounds of 3,4,9,10-perylenetetracarboxylic acid, as well as for dyeing and printing of textile materials with the formation, on the material, of asymmetric compounds of 3,4,9,10-perylenetetracarboxylic acid having the following formula:

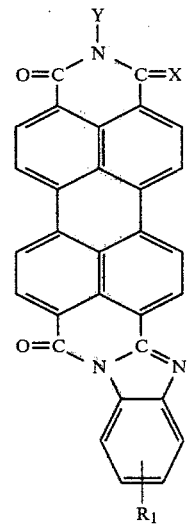

wherein $R_1$ is hydrogen, halogen, or alkyl; when X is oxygen, Y is hydrogen, alkyl, cycloalkyl, or aryl containing at least one substituent from the group including; halogen, alkyl, or alkoxy, when X is nitrogen, Y is

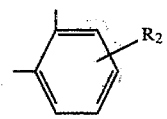

where $R_2$ is hydrogen, halogen, or alkyl; Y being linked with X to form a benzimidazole cycle.

The compounds according to the present invention dye textile materials to various shades of violet color.

1 Claim, No Drawings

1-1-BINAPHTHYL-4,4′,5,5′,8,8′-HEXACARBOXYLIC ACID COMPOUNDS, METHOD OF PREPARATION AND USE THEREOF FOR THE SYNTHESIS OF ASYMMETRIC DERIVATIVES OF 3,4,9,10-PERYLENETETRACARBOXYLIC ACID, AND FOR DYEING AND PRINTING OF TEXTILE MATERIALS

FIELD OF THE INVENTION

The present invention relates to the art of organic dyestuffs and, more specifically, to novel compounds—1,1′-binaphthyl-4,4′,5,5′,8,8′-hexacarboxylic acid derivatives, a method for preparing said compounds and their use.

The compounds according to the present invention belong to a new class of water-soluble dyestuffs that form, directly on the fiber, water-insoluble asymmetric derivatives of perylenetetracarboxylic acid. They are useful in dyeing and printing textile materials.

BACKGROUND OF THE INVENTION

Known in the art are symmetric derivatives of 1,1′-binaphthyl-4,4′,5,5′,8,8′-hexacarboxylic acid, specifically diimides or dibenzimidazoles which are obtained by condensation of 1,1′-binaphthyl-4,4′,5,5′,8,8′-hexacarboxylic acid dianhydride with amines or ortho-diamines(cf. USSR Inventor's Certificate No. 366705). Diimides of 1,1′-binaphthyl-4,4′-5,5′,8,8′-hexacarboxylic acid dye textile materials to various shades of red color, while dibenzimidazoles of 1,1′-binaphthyl-4,4′,5,5′,8,8′-hexacarboxylic acid dye textile materials to blue and blue-violet colors. The resulting dyed materials are fast to all kinds of processing and light.

SUMMARY OF THE INVENTION

It is an object of the present invention to broaden the color range of dyestuffs.

In accordance with the present invention, this object is accomplished by providing of novel compounds of 1,1′-binaphthyl-4,4′,5,5′,8,8′-hexacarboxylic acid having the formula:

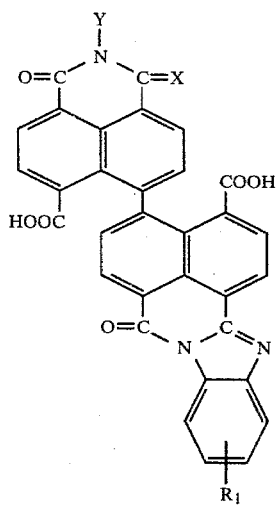

(I)

wherein $R_1$ is hydrogen, halogen, or alkyl; when X is oxygen, Y is hydrogen, alkyl, cycloalkyl, or an aryl containing at least one substituent from the group including: halogen, alkyl, or alkoxy; when X is nitrogen, Y is

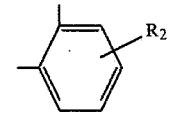

(II)

wherein $R_2$ is hydrogen, halogen, or alkyl; Y being linked to X with the formation of a benzimidazole cycle.

The compounds of the above-given formula are yellow crystalline substances that do not melt at a temperature of 300° C., and are sparingly soluble in water, but form water soluble salts upon interaction with basic compounds. The compounds according to the present invention also are dyestuffs for textile materials and dye same to various shades of violet color.

The object of the present invention is also accomplished by providing a method for preparing derivatives of 1,1′-binaphthyl-4,4′,5,5′,8,8′-hexacarboxylic acid, wherein, according to the present invention, 1,1′-binaphthyl-4,4′-5,5′,8,8′-hexacarboxylic acid anhydride is treated with sodium hydroxide or potassium hydroxide; the resulting hexapotassium or hexasodium salt of 1,1′-binaphthyl-4,4′-5,5′,8,8′-hexacarboxylic acid is condensed upon heating at reflux at a pH of from 6.3 to 6.8 which is maintained by adding a mineral or organic acid, with ortho-phenylenediamines of the formula:

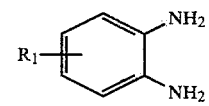

(III)

wherein $R_1$ is hydrogen, halogen, or alkyl; the resulting benzimidazole-1,1′-binaphthyl-4,4′,5,5′,8,8′-hexacarboxylic acid anhydride of the formula:

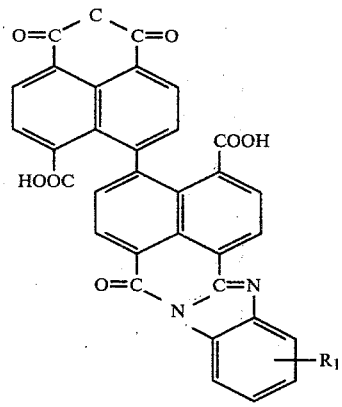

(IV)

wherein $R_1$ is hydrogen, halogen, or alkyl; is recovered and condensed with an amine of the formula:

$R_3$—NH$_2$ 

wherein $R_3$ is hydrogen, alkyl, cycloalkyl, or aryl containing at least one substituent from the group including: halogen, alkyl, or alkoxy; or with ortho-phenylenediamines of the formula:

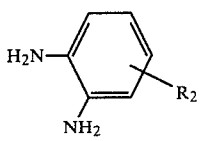

wherein $R_2$ is hydrogen, alkyl, or halogen; in an excess of said amine, in water or in an organic solvent, followed by isolation of the desired product.

To improve the quality of the product, it is advisable to isolate benzimidazole-1,1'-binaphthyl-4,4',5,5',8,8'-hexacarboxylic acid anhydride of formula (IV) by alkalinizing the reaction mass to a pH value of from 9.0 to 9.5.

The present invention also relates to the use of the novel compounds of 1,1'-binaphthyl-4,4',5,5',8,8'-hexacarboxylic acid.

One of the applications is a process for producing derivatives of 3,4,9,10-perylenetetracarboxylic acid, wherein, according to the present invention 1,1'-binaphthyl-4,4',5,5',8,8'-hexacarboxylic acid compounds of formula (I) are treated with a reducing agent comprising sodium hydrosulphite or rongalite in an alkaline medium, followed by oxidation to give, the above-mentioned asymmetric compounds of the formula:

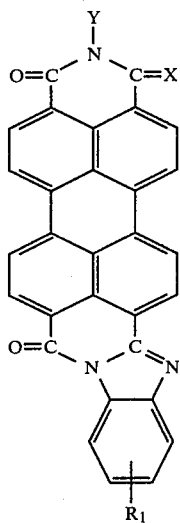

wherein $R_1$ is hydrogen, halogen, or alkyl; when X is oxygen, Y is hydrogen, alkyl, cycloalkyl, or aryl containing at least one substituent from the group including: halogen, alkyl, or alkoxy; when X is nitrogen, Y is

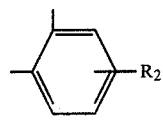

(II), wherein $R_2$ is hydrogen, halogen, or alkyl; Y being linked to X with the formation of a benzimidazole cycle.

The resulting compounds of 3,4,9,10-perylenetetracarboxylic acid can be used as pigments.

Another application of the compounds of formula (I) is a process for dyeing textile materials, wherein, according to the present invention, the textile material is impregnated with an aqueous alkaline solution of compounds of formula (I) in the presence of a reducing agent which is sodium hydrosulphite or rongalite, followed by oxidation to give asymmetric compounds of 3,4,9,10-perylene tetracarboxylic acid of formula (VI) on the material.

Still another application of the compounds of 1,1'-binaphthyl-4,4',5,5',8,8'-hexacarboxylic acid is a process for printing of textile materials, wherein according to the present invention, a printing paste is applied onto the material consisting of compounds of 1,1'-binaphthyl-4,4',5,5',8,8'-hexacarboxylic acid according to formula (I), an alkaline agent, a reducing agent such as sodium hydrosulphite or rongalite, whereafter the material is subjected to heat-treatment with subsequent oxidation to give asymmetric compounds of 3,4,9,10-perylenetetracarboxylic acid of formula (VI).

DETAILED DESCRIPTION OF THE INVENTION

The method for preparing compounds of 1,1'-binaphthyl-4,4',5,5',8,8'-hexacarboxylic acid according to the present invention is carried out in the following manner.

The process is conducted in two stages. In the first stage benzimidazole-1,1'-binaphthyl-4,4'-5,5',8,8'-hexacarboxylic acid anhydride of the formula (IV) is produced. In the second stage, the resulting compound is condensed with amines or ortho-phenylenediamines different from those employed in the first stage. The first stage of the process is performed as follows.

1,1'-Binaphthyl-4,4',5,5',8,8'-hexacarboxylic acid anhydride is converted to a hexapotassium or hexasodium salt by dissolution in an aqueous solution of an alkali. This salt is condensed with ortho-phenylenediamines of formula (III) at a pH of from 6.3 to 6.8. At a pH below 6.3 the yield of corresponding dibenzimidazoles of 1,1'-binaphthyl-4,4',5,5',8,8'-hexacarboxylic acid is sharply increased, while at pH above 6.8 the reaction proceeds very slowly.

The reaction is completed substantially within 15 hours at the boiling point (107°–108° C.). The predetermined pH value is maintained by the addition of a mineral acid or an organic acid.

The addition of salts (NaCl or KCl) facilitates precipitation of benzimidazole-1,1'-binaphthyl-4,4',5,5',8,8'-hexacarboxylic acid or its derivatives, thus increasing its yield. Upon alkalinization of the reaction mass to the pH of 9.0 to 9.5, benzimidazole of 1,1'-binaphthyl-4,4',5,5',8,8'-hexacarboxylic acid passes into solution, whereas dibenzimidazole of 1,1'-binaphthyl-4,4',5,5',8,8'-hexacarboxylic acid (by-product) remains in the precipitate and can be separated by filtration. From the filtrate, benzimidazole-1,1'-binaphthyl-4,4',5,5',8,8'-hexacarboxylic acid anhydride of formula (IV) is recovered by acidification.

In the second stage the recovered compound of the formula (IV) is condensed with an amine of the formula: $R_3$—$NH_2$, wherein $R_3$ is hydrogen, alkyl, cycloalkyl, or aryl containing at least one substituent from the group including: halogen, alkyl, or alkoxy, or with ortho-phenylenediamines of the formula (V) in an excess of the above-mentioned amine, in water or in an organic solvent such as acetic acid, dimethylformamide, or trichlorobenzene. The thus-prepared dyestuffs are separated from the reaction mass by conventional techniques, for example by filtration.

Dyeing of textile materials, for example cotton, linen, viscose, staple, acetate, polyamide materials with the dyes of the present invention is effected in an alkaline medium upon the action of reducing agents such as sodium hydrosulphite or rongalite, followed by oxidation to convert the derivatives of 1,1'-binaphthyl-4,4',5,5',8,8'-hexacarboxylic acid to corresponding symmetric derivatives of 3,4,9,10-perylenetetracarboxylic acid with the formation of dyeings of red-violet, violet and blue-violet colors with various shades on the material.

The dyestuffs according to the present invention are employed for printing on textile materials by way of application, onto the material, of a printing ink containing the derivatives of the formula (I), an alkaline agent, a thickener, a reducing agent—sodium hydrosulphite or rongalite, whereafter the material is dried, maintained in an atmosphere of saturated steam at a temperature of from 101° to 105° C. and subjected to oxidation.

Corresponding asymmetric compounds of 3,4,9,10-perylenetetracarboxylic acid can be obtained from the dyestuffs according to the present invention not only on fiber, but in a reaction apparatus as well, and they can be employed as they are, for example as pigments. It should be noted that the resulting asymmetric derivatives of 3,4,9,10-perylenetetracarboxylic acid are novel compounds hitherto unknown in the literature. Their preparation from 3,4,9,10-perylenetetracarboxylic acid dianhydride is very difficult.

The dyestuffs according to the present invention have a number of advantages over the existing violet vat dyestuffs such as vat violet 9 (Color Index 60005) and vat violet 1 (Color Index 60010). Solubility of the dyestuffs according to the present invention substantially simplifies their use, and makes it possible to avoid non-uniformity of dyeing. Furthermore, in the use of such dyes the rate of consumption of alkaline and reducing agents are considerably reduced (by 2–6 times) as compared to vat dyestuffs. There is no need in the manufacture of special preparative forms as with vat dyestuffs. It should also be noted that the dyestuffs according to the present invention give dyeings that are not sensitive to water drops.

For a better understanding of the present invention, some specific examples are give hereinbelow by way of illustration.

EXAMPLE 1

12.05 g (0.023 g-mol) of a 92% 1,1'-binaphthyl-4,4',5,5',8,8'-hexacarboxylic acid anhydride and 8 g of caustic soda are dissolved in 75 ml of water, heated to reflux and maintained for 30 minutes. There are added 17.5 g of sodium chloride and 2.7 g (0.025 g-mol) of ortho-phenylenediamine. Thereafter, the reaction mass is acidified with a 15% solution of hydrochloric acid to pH=6.3, and allowed to stand for 15 hours at a temperature of 108° C. and pH of from 6.3 to 6.8. The pH value is maintained by the addition of a 15% solution of hydrochloric acid. On completion of the residence the mass is alkalinized to reach a pH of 9.0 and dibenzimidazole-1,1'-binaphthyl-4,4',5,5',8,8'-hexacarboxylic acid is filtered-off. Anhydride of benzimidazole—1,1'-binaphthyl-4,4',5,5',8,8'-hexacarboxylic acid is recovered from the filtrate by acidifying with acetic acid in the amount of 6.41 g (46.3% by weight). After crystallization from acetic anhydride 6.00 g (43.3% by weight) of the product are obtained.

Found, %: C 69.50; 69.40; H 2.57, 2.58; N 5.23, 5.05 $C_{32}H_{14}N_2O_8$. Calculated, %: C 69.32; H 2.55; N 5.05.

Thereafter, 6.00 g (0.0108 g-mol) of anhydride of benzimidazole 1,1'-binaphthyl-4,4',5,5',8,8'-hexacarboxylic acid are charged into 75 ml of cyclohexylamine, kept for 3 hours at reflux. Then the reaction mass is cooled and poured into 150 ml of 15% hydrochloric acid. The precipitate is filtered-off, washed with water and dried to give 6.48 g (94% by weight) of N-cyclohexylimide of benzimidazole-1,1'-binaphthyl-4,4',5,5',8,8'-hexacarboxylic acid. Recrystallization is effected from dimethylformamide.

Found, %: N 6.25; 6.50. $C_{38}H_{25}N_3O_7$. Calculated, %: N 6.61.

Then 0.2 g of the resulting N-cyclohexylamide of benzimidazole-1,1'-binaphthyl-4,4',5,5',8,8'-hexacarboxylic acid is dissolved in 100 ml of 1% caustic soda, 1 g of sodium hydrosulphite is added thereto and into the reaction mixture a sample of cotton fabric weighing 5 g is immersed. The dyeing solution is heated to a temperature of 80° C. and kept at this temperature for about one hour. Then the fabric sample is washed with cold water until a bright violet dyeing is formed thereon.

A mixture consisting of 1.00 g of N-cyclohexylimide of benzimidazole-1,1'-binaphthyl-4,4',5,5',8,8'-hexacarboxylic acid, 4.0 g of glycerol, 30 g of starch-tragacanth thickener, 5.0 g of potassium carbonate, 5.0 g of rongalite and 5 ml of water are applied onto a cotton fabric and dried.

The dried fabric is kept in an atmosphere of saturated steam at a temperature of from 101° to 105° C. for 5 minutes, whereafter the fabric is oxidized, thoroughly washed with water, and soap depending on the vat dye type. A bright violet dyeing remains on the fabric.

A solution of 4.00 g of N-cyclohexylimide of benzimidazole-1,1'-binaphthyl-4,4',5,5',8,8'-hexacarboxylic acid in 100 ml of a 5% solution of caustic soda, was charged with 2–3 g of sodium hydrosulphite, and maintained at a temperature of 80° C. for about one hour. The solution of the leuco-compound is oxidized by purging air therethrough for two hours. The precipitate is filtered-off, washed with a 1% soda solution, then with water and dried. 2.62 g (76.2%) of N-cyclohexylimide of benzimidazole-3,4,9,10-perylenetetracarboxylic acid are obtained.

Found, %: N 7.85, 7.70. $C_{36}H_{23}N_3O_3$. Calculated, %: N 7.72

EXAMPLE 2

2.00 g (0.0036 g-mol) of benzimidazole-1,1'-binaphthyl-4,4',5,5',8,8'-hexacarboxylic acid anhydride produced as in Example 1 are suspended in 15 ml of dimethylformamide charged with 7.00 g of p-bromoaniline and refluxed at a temperature of 153° C. for two hours. After cooling 5 ml of water are added, and the residue is filtered-off, washed with 60% aqueous dimethylformamide and dried to give 2.00 g (78.2% by weight) of N-(4-bromophenyl)-imide of benzimidazole-1,1'-binaphthyl-4,4',5,5',8,8'-hexacarboxylic acid. Crystallization is effected from acetic anhydride.

Found, %: Br 11.00, 11.28. $C_{38}H_{12}BrN_3O_7$. Calculated, %: Br 11.28.

The resulting compound is employed for dyeing and printing in a manner similar to that described in Example 1.

N-(4-bromophenyl)-imide of benzimidazole-3,4,9,10-perylenetetracarboxylic acid is obtained in a manner similar to that described in Example 1 in a yield of 70% by weight.

Found, %: N 6.85; 6.90. $C_{36}H_{18}BrN_3O_3$. Calculated, %: N 6.80.

EXAMPLE 3

In 40 ml of glacial acetic acid there are introduced 2.00 g (0.0036 g-mol) of benzimidazole-1,1'-binaphthyl-4,4'-5,5'8,8'-hexacarboxylic acid anhydride prepared as in Example 1 and 1.50 g (0.0105 g-mol) of 4-chloro-1,2-phenylenediamine that are refluxed for 6 hours, and cooled. The precipitate is filtered-off and washed with water and then dried to give 2.03 g (83.3% by weight) of 5"(6")chlorodibenzimidazole-1,1'-binaphthyl-4,4',5,5',8,8'-hexacarboxylic acid. The product is crystallized from a 1% solution of sodium bicarbonate.

Found, %: Cl 5.30; 5.27; N 8.28, 8.50. $C_{36}H_{15}ClN_4O_2$. Calculated, %: Cl 6.21; N 9.81.

EXAMPLE 4

Into 40 ml of a 25% aqueous solution of ammonia there are charged 2.00 g (0.0036 g-mol) of benzimidazole-1,1'-binaphthyl-4,4',5,5',8,8'-hexacarboxylic acid anhydride prepared as in Example 1, heated to reflux and maintained for two hours, filtered-off and dried to give 1.50 g (75% by weight) of benzimidazole-1,1'-binaphthyl-4,4',5,5',8,8'-hexacarboxylic acid imide. The resulting compound is crystallized from dimethylformamide.

Found, %: N 7.63; 7.68, $C_{32}H_{15}N_3O_7$. Calculated, %: N 7.59.

Dyeing and printing with the thus-prepared compound are effected in a manner similar to that described in Example 1 hereinbefore.

Benzimidazole-3,4,9,10-perylenetetracarboxylic acid imide is produced following the procedure described in Example 1 with a yield of 96.0% by weight.

Found, %: N 9.00, 9.10. $C_{30}H_{13}N_3O_3$. Calculated, %: N 9.07.

EXAMPLE 5

To an aqueous suspension of 5.57 g (0.01 g-mol) of benzimidazole-1,1'-binaphthyl-4,4',5,5',8,8'-hexacarboxylic acid anhydride prepared as in Example 1 there is added 1.3 ml (0.012 g-mol) of m-toluidine and maintained for 10 hours. The precipitate is filtered-off, dissolved in 30 ml of a 1% alkali solution, then acidified with concentrated hydrochloric acid. The precipitate is filtered-off, washed with water and dried. 4.50 g (70% by weight) of N-(3-tolyl)-imide of benzimidazole-1,1'-binaphthyl-4,4',5,5',8,8'-hexacarboxylic acid are obtained. The product is crystallized from acetic anhydride.

Found, %: N 6.42, 6.45. $C_{39}H_{21}N_3O_7$. Calculated, %: N 6.52.

Dyeing and printing with the resulting compound are effected in a manner similar to that described in Example 1.

N-(3-tolyl)-imide of benzimidazole-3,4,9,10-perylenetetracarboxylic acid is prepared following the procedure similar to that described in Example 1 with a yield of 87.1% by weight.

Found, %: N 7.07; 6.79. $C_{37}H_{19}N_3O_3$. Calculated, %: N 7.59.

EXAMPLE 6

To an aqueous suspension of 5.57 g (0.01 g-mol) of benzimidazole-1,1'-binaphthyl-4,4',5,5',8,8'-hexacarboxylic acid anhydride prepared as in Example 1 at a temperature of 20° C. there are added 1.48 g (0.012 g-mol) of p-xylidine and the suspension is maintained at reflux for 10 hours. The precipitate is filtered-off, dissolved in 30 ml of a 1% solution of sodium hydroxide, acidified with a concentrated hydrochloric acid. The precipitate is filtered-off, washed with water and dried.

There are obtained 4.28 g (65% by weight) of N-(2,4-dimethylphenyl)-imide of benzimidazole-1,1'-binaphthyl-4,4'-5,5'-8,8'-hexacarboxylic acid which is crystallized from dimethylformamide.

Found, %: N 6.28, 6.30. $C_{40}H_{23}N_3O_7$. Calculated, %: N 6.38.

N-(2,4-dimethylphenyl)imide of benzimidazole-3,4,9,10-perylenetetracarboxylic acid is produced in a yield of 85.0% by weight in a manner similar to that described in Example 1.

Found, %: N 7.45, 7.35. $C_{38}H_{21}N_3O_3$. Calculated, %: N 7.40.

EXAMPLE 7

12.05 g (0.023 g-mol) of a 92% 1,1'-binaphthyl-4,4',5,5',8,8'-hexacarboxylic acid and 11.2 g of caustic soda are dissolved in 75 ml of water, heated to reflux and maintained for 30 minutes.

Added to the above are 17.5 g of sodium chloride, and 3.56 g (0.025 g-mol) of 4-chloro-12-phenylenediamine, which are acidified with a 30% aqueous solution of acetic acid to a pH of 6.5. The reaction mixture is maintained for 15 hours at a temperature of 108° C. and pH of from 5.6 to 6.8. The required pH value is maintained by the addition of a 15% solution of hydrochloric acid. On completion of the residence, the reaction mass is alkalinized to a pH of 9.3, dichlorodibenzimidazole-1,1'-binaphthyl-4,4'5,5',8,8'-hexacarboxylic acid is filtered-off, 5"-chlorobenzimidazole-1,1'-binaphthyl-4,4',5,5',8,8'-hexacarboxylic acid anhydride is separated from the filtrate by acidification with acetic acid. The product amount is 4.88 g (35% by weight).

Found, %: C 64.77, 64.89; H 2.66, 2.66; N 4.75, 4.90 $C_{32}H_{13}ClN_2O_8$. Calculated, %: C 65.53, H 2.23; N 4.76.

Found, %: Cl 6.09; 6.10. Calculated, %: Cl 6.09.

Into 34 ml of butylamine there are introduced 4.88 g (0.00334 g-mol) of 5"-chlorobenzimidazole-1,1'-binaphthyl-4,4',5,5',8,8'-hexachlorocarboxylic acid anhydride, that are heated to reflux and maintained for 3 hours. The reaction mass is then cooled and poured into 73 ml of 15% hydrochloric acid. The precipitate is filtered-off and dried to give 4.98 g (93% by weight) of N-butylimide of 5"-(6")-chlorobenzimidazole-1,1'-binaphthyl-4,4',5,5',8,8'-hexacarboxylic acid. Recrystallization is effected from dimethylformamide.

Found, %: N 5.47, 5.50. $C_{36}H_{22}ClN_3O_7$. Calculated, %: N 5.38.

Dyeing and printing by means of the thus-prepared compound is effected following the procedure described in Example 1 hereinbefore.

N-Butylimide of 5"(6")-chlorobenzimidazole-3,4,9,10-perylenetetracarboxylic acid is prepared as described in Example 1 in a yield of 95% by weight.

Found, %: N 7.60, 7.65; Cl 6.42, 6.45. $C_{34}H_{20}ClN_3O_3$. Calculated, % N 7.58, Cl 6.40.

EXAMPLE 8

Into 14 ml of butylamine there are introduced 2.00 g (0.0036 g-mol) of benzimidazole-1,1'-binaphthyl-4,4',5,5',8,8'-hexacarboxylic acid anhydride prepared as in Example 1. The reaction mixture is maintained at reflux for 3 hours. The precipitate is filtered-off, dried to give 2.55 g (95% by weight) of N-butylimide of benzimidazole-1,1'-binaphthyl-4,4',5,5',8,8'-hexcarboxylic acid which is then recrystallized from dimethylformamide.

Found, %: N 5.70, 5.62. $C_{36}H_{23}N_3O_7$. Calculated, %: N 5.64.

Dyeing and printing by means of the resulting compound are effected as described in Example 1.

N-Butylimide of benzimidazole-3,4,9,10-perylenetetracarboxylic acid is prepared in a manner similar to that described in Example 1 in the yield of 95% by weight.

Found, %: N 7.79, 8.10. $C_{34}H_{21}N_3O_3$. Calculated, %: N 8.09.

EXAMPLE 9

12.05 g (0.023 g-mol) of a 92% 1,1'-binaphthyl-4,4'-5,5',8,8'-hexacarboxylic acid and 8 g of caustic soda are dissolved in 75 ml of water, heated to reflux and maintained for 30 minutes at this temperature, then loaded with 17.5 g of sodium chloride and 3.05 g of 4-methyl-1,2-phenylenediamine. The reaction mixture is acidified with a 15% solution of hydrochloric acid to a pH of 6.8, kept for 15 hours at the temperature of 108° C. and pH of 6.8. The required pH value is maintained by the addition of a 15% solution of hydrochloric acid. On completion of the residence, the reaction mass is alkalinized to a pH of 9.5. The product, i.e. dimethylbenzimidazole-1,1'-binaphthyl-4,4',5,5',8,8'-hexacarboxylic acid, is separated by filtration. From the filtrate 5"-(6")-methyl-benzimidazole-1,1'-binaphthyl-4,4',5,5',8,8'-hexacarboxylic acid anhydride is isolated by acidification with acetic acid. The product yield is 5.49 g (37.3% by weight).

Found, %: C 69.52, 69.60; H 2.77, 2.78; N 4.90, 4.97. $C_{35}H_{16}N_2O_8$. Calculated, %: C 69.72; H 2.84; N 4.93.

Thereafter 5.49 g (0.0983 g-mol) of 5"(6")-methylbenzimidazole-1,1'-binaphthyl-4,4',5,5',8,8'-hexacarboxylic acid anhydride are charged into 28 ml of p-phenetidine, maintained at a temperature of 150° C. for two hours, cooled and poured onto 85 ml of a 15% solution of hydrochloric acid. The precipitate is filtered-off, washed with water and dried to give 6.73 g (91% by weight) of N-(4-ethoxyphenyl)-imide of 5"(6")-methyl-benzimidazole-1,1'-binaphthyl-4,4',5,5',8,8'-hexacarboxylic acid which is crystallized from acetic anhydride.

Found, %: N 6.03, 6.15. $C_{41}H_{25}N_3O_8$. Calculated, %: N 6.11.

Dyeing and printing by means of the thus-prepared compound is effected following the procedure described in the foregoing Example 1.

N-4-ethoxyphenylimide of 5"(6")-methylbenzimidazole-3,4,9,10-perylenetetracarboxylic acid is produced following the procedure of Example 1 in a yield of 80% by weight.

Found, %: N 6.85, 7.00. $C_{39}H_{23}N_3O_4$. Calculated, %: N 7.03.

EXAMPLE 10

The process is carried out in a manner similar to that described in Example 9, except that the first condensation is effected using 4-ethyl-1,2-phenylenediamine. There is obtained N-(4-ethoxyphenyl)-imide of 5"(6")-ethylbenzimidazole 1,1'-binaphthyl-4,4',5,5',8,8'-hexacarboxylic acid.

Found, %: N 6.05, 60.1. $C_{42}H_{27}N_3O_8$. Calculated, %: N 5.99.

Dyeing and printing are effected following the procedure of Example 1. N-(4-ethoxyphenyl)-imide of 5"(6")-ethylbenzimidazole-3,4,9,10-perylenetetracarboxylic acid is prepared as in Example 1, the yield is 80% by weight.

Found, %: N 6.90, 6.95. $C_{40}H_{25}N_3O_4$. Calculated, %: N 6.87.

EXAMPLE 11

The process is carried out following the procedure of Example 7, except that the first condensation is effected using 4-bromo-1,2-phenylenediamine.

Dyeing and printing are performed as in Example 1.

Butylimide of 5"(6")-bromobenzimidazole-3,4,9,10-perylenetetracarboxylic acid is prepared following the procedure similar to that of Example 1; the product yield is 90.0% by weight.

Found, %: N 7.25, 7.115; Br 13.25, 13.30. $C_{34}H_{20}BrN_3O_3$. Calculated, %: N 7.02, Br 13.35.

EXAMPLE 12

To 40 ml of a 25% aqueous solution of methylamine there are charged 2.00 g (0.0036 g-mol) of benzimidazole-1,1'-binaphthyl-4,4',5,5',8,8'-hexacarboxylic acid anhydride prepared as in Example 1, heated to reflux and maintained for two hours, then filtered, dried to give 1.64 g (80%) of N-methylimide of benzimidazole-1,1'-binaphthyl-4,4',5,5',8,8'-hexacarboxylic acid. The product is crystallized from acetic anhydride.

Found, %: N 7.35, 7.40. $C_{33}H_{17}N_3O_7$. Calculated, %: N 7.40.

Dyeing and printing is effected as described in the foregoing Example 1.

N-Methylimide of benzimidazole-3,4,9,10-perylenetetracarboxylic acid is prepared as described in Example 1, the yield is 97.0% by weight.

Found, %: N 8.90, 8.85. $C_{31}H_{15}N_3O_3$. Calculated, %: N 8.81.

What is claimed is:

1. 1,1'-binaphthyl-4,4',5,5',8,8'-hexacarboxylic acid compounds of the formula:

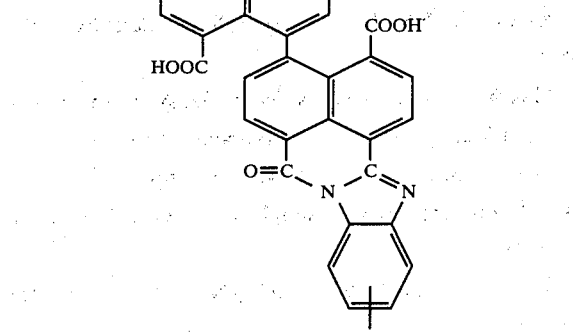
wherein $R_1$ is selected from the group consisting of hydrogen, halogen, or alkyl; X is oxygen; and Y is selected from the group consisting of hydrogen, alkyl, cycloalkyl, or an aryl containing at least one substituent selected from the group consisting of halogen, alkyl, or alkoxy.
* * * * *